United States Patent [19]
Cohen et al.

[11] Patent Number: 6,132,952
[45] Date of Patent: Oct. 17, 2000

[54] STORAGE SYSTEM COMPRISING AN EMPTIED ZONA PELLUCIDA AND SPERMATOZOA PLACED THEREIN AND A METHOD OF CRYOPRESERVATION

[75] Inventors: Jacques Cohen, Mountain Lakes, N.J.; Steen Willadsen, Windmere, Fla.

[73] Assignee: Saint Barnabas Medical Center, Livingston, N.J.

[21] Appl. No.: 09/088,392

[22] Filed: Jun. 1, 1998

Related U.S. Application Data

[60] Provisional application No. 60/047,934, May 30, 1997.

[51] Int. Cl.[7] .............................. A01N 1/02; A61B 17/43
[52] U.S. Cl. .................................................. 435/2; 600/33
[58] Field of Search ................................... 435/2; 600/33

[56] References Cited

U.S. PATENT DOCUMENTS

| | | | |
|---|---|---|---|
| 4,801,689 | 1/1989 | Oikawa | 530/395 |
| 4,847,363 | 7/1989 | Oikawa | 530/395 |
| 5,272,086 | 12/1993 | Pineda et al. | 435/284 |

OTHER PUBLICATIONS

Cohen et al., "Cryopreservation of Single Human Spermatozoa", Human Reproduction 12 (May 5) : 994–1001 (1997).

Turek et al., "Cryopreservation and recover of motile, aspirated human sperm within biopsy capsules from hamster eggs", J. Andrology (Jan.–Feb. 1998) No. Suppl. p. 42. 23rd Meeting Am. Soc. Androl. Mar. 26–29, 1998.

Palermo, GD et al "Intracytoplasmic Sperm Injection: A Novel Treatment for all Forms of Male Factor Infertility," Fertil. Steril., 63, 1231–1240 (1995).

Silber, S.J. et al "High Fertilization and Pregnancy Rate After Intracytoplasmic Sperm Injection With Spermatozoa From Testicle Biopsy", Hum. Reprod., 10, 148–152 (1995a).

Palermo, G et al "Pregnancies After Intracytoplasmic Sperm Injection of Single Spermatozoon into an Oocyte", Lancet, 340, 17–18 (1992).

Craft, I et al "Fertilising Ability of Testicular Spermatozoa", Lancet, 342, 864 (1992).

Schoysman, R. et al "Successful Fertilization by Testicular Spermatozoa in an In–vitro Fertilization Programme", Hum. Repro, 8, 1339–1340 (1993).

Silber, S. J et al "The Use of Epididymal and Testicular Spermatzoa for Intracytoplasmic Sperm Injection: The Genetic Implications for Male Infertility", Hum. Reprod., 10, 2031–2043(1995b).

Devroey, P. et al, "Pregnancies After Testicular Sperm Extraction and Intra–Cytoplasmic Sperm Injection in Non–Obstructive Azoospermia", Hum Reprod, 10, 1457–1460 (1995).

Hewitt, J. et al "Cryopreservation of Semen in Patients With Malignant Disease: Role of In Vitro Fertilization", Lancet, 2, 446–447 (1955).

Willadsen, S.M. "Nuclear Transplantation in Sheep", Nature, 320:63 (1986).

Podsiadly, B.T. et al., "Case Report Pregnancy Resulting From Intracytoplasmic Sperm Injection of Cryopreserved Spermatozoa Recovered From Testicular Biopsy", Human Reprod. 11, 1306–1308 (1996).

Wassarman, P.M., "Profile of a Mammalian Sperm Receptor", Development 198, 1–17 (1990).

Florman HM et al "O–linked Oligosaccharides of Mouse Egg ZP3 Account for its Sperm Receptor Activity", Cell 41, 313–324 (1985).

Rosiere TK et al., "Identification of a Region Mouse Zona Pellucida Glycoprotein MZP3 That Possess Sperm Receptor Activity", Dev Biol 154, 309–317 (1992).

Bleil JD et al., "Sperm–Egg Interactions in the Mouse: Sequence of Events and Induction of the Acrosome Reaction by a Zona Pellucida Glycoprotein", Dev. Biol 95, 317–324 (1983).

Bleil JD et al., "Identification of a Secondary Sperm Receptor in the Mouse Egg Zona Pellucida: Role for Maintenance of Binding of Acrosome Reacted Sperm to Eggs", Dev. Biol 128, 376–385 (1988).

Bleil JD et al., "Mammalian Sperm–Egg Interaction: Identification of a Glycoprotein in Mouse Egg Zonae Pellucidae Possessing Receptor Activity for Sperm", Cell 20, 873–882 (1980).

Miller DJ et al., "Egg Cortical Granule N–Acetylgucosaminidase is Required for the Mouse Zona Block to Polyspermy", J Cell Biol 123, 1431–1440 (1993).

Bleil JD et al., "Autoradiographic Visualization of the Mouse Egg's Sperm Receptor Bound to Sperm", J Cell Biol 102, 1363–1371 (1986).

Moller CC et al., "Characterization of a Proteinase That Cleaves Zona Pellucida Glycoprotein ZP2 Following Activation of Mouse Eggs", Dev Biol 132, 102–112 (1989).

Bleil JD et al., "Mammalian Sperm–Egg Interaction: Fertilization of Mouse Eggs Triggers Modification of the Major Zona Pellucida Glycoprotein ZP2" Dev Biol 86, 189–197 (1981).

(List continued on next page.)

*Primary Examiner*—Sandra E. Saucier
*Attorney, Agent, or Firm*—Milde, Hofferberg & Macklin, LLP

[57] ABSTRACT

A procedure for cryopreservation and efficient post-thaw recovery of a single or few cells, preferably human spermatozoa, their precursor cells or blastomeres, which is achieved by injecting cells into cell-free mammalian zonae pellucidae. The cells may also be of any other type where there are provided a relatively small number of valuable cells which must be retrieved. The zona pellucida may be cryopreserved with the cells contained therein. The method involves a combination of physical micromanipulation procedures and cryoprotectant mediated cryopropreservation. The zonae may be tracked by positioning them into straws between two small air bubbles prior to preservation. There is a high recovery of zonae and sperm within the zonae, and a high fertilization rate of the sperm using ICSI after recovery.

25 Claims, 2 Drawing Sheets

(2 of 2 Drawing Sheet(s) Filed in Color)

OTHER PUBLICATIONS

Bercegeay S et al., "Composition of Human Zona Pellucida as Revealed by SDS–Page After Silver Staining", Mol Reprod Dev 41, 355–359 (1995).

Moos, J et al., "Composition of the Human Zona Pellucida and Modifications Following Fertilization", Hum Reprod 10, 2467–2471 (1995).

Naz R K et al., "Molecular Identities of Human Sperm Proteins That Bind Human Zona Pellucide: Nature of Sperm–zona Interaction, Tyrosine Kinase Activity, and Involvement of FA–1", Mol Reprod Dev 39, 397–408(1994).

Shabanowitz RB et al., "Characterization of the Human Zona Pellucida From Fertilizaed and Unfertilized Eggs" J Reprod Fert 82, 151–161 (1988).

Shabanowitz RB et al., "Mouse Antibodies to Human Zona Pellucida: Evidence That Human ZP3 is Strongly Immunogenic and Contains Two Distinct Isomer Chains", Biol Reprod 43, 260–270(1990).

Morales, P et al., "Interaction of Human Spermatozoa With the Zona Pellucida of Oocyte: Development of the Acrosome Reaction", Frontiers in Bioscience 1, d 146–160 (Aug. 1, 1995).

Palermo, G. et al., "The Human Zygote Inherits its Mitotic Potential From the Male Gamete", Hum Reprod., 9, 1220–1225 (1994).

Jarow, J. "Intratesticular Arterial Anatomy", J. Androl, 11, 255–259 (1990).

Patrizio, P. et al., "Successful Fertilization, Pregnancy, and Birth Using Epididymal Sperm Frozen 24 Hours After Conventional Oocyte Insemination", Fertil. Steril, 64, 863–865 (1995).

STORAGE SYSTEM COMPRISING AN EMPTIED ZONA PELLUCIDA AND SPERMATOZOA PLACED THEREIN AND A METHOD OF CRYOPRESERVATION

The present application claims benefit of priority for U.S. Provisional Patent Application Ser. No. 60/047,934 filed on May 30, 1997.

FIELD OF THE INVENTION

The present invention relates to the field of cryopreservation techniques, and more particularly to cryopreservation techniques for single cell samples. The invention also relates to methods for manipulating a zona pellucida, the manipulated empty zona pellucida itself and methods of use therefore.

BACKGROUND OF THE INVENTION

The outlook and treatment of adverse human gamete interaction has drastically changed with the advent of intracytoplasmic sperm injection (ICSI) and manipulation of enriched but often poor sperm suspensions, sometimes yielding less than double digit counts. Palermo G D, Cohen J, Alikani M, Adler A, and Rosenwaks, Z., "Intracytoplasmic sperm injection: a novel treatment for all forms of male factor infertility", *Fertil. Steril.*, 63, 1231–1240 (1995); Silber, S. J., Van Steirteghem, A. C., Liu, J., Nagy, Z., Tournaye, H. and Devroey, P., "High fertilization and pregnancy rate after intracytoplasmic sperm injection with spermatozoa from testicle biopsy", *Hum. Reprod.*, 10, 148–152 (1995a).

Men who are azoospermic can now be treated using surgical isolation of sperm cells from their testicles or reproductive tract. Palermo, G., Joris, H., Devroey, P., and Van Steirteghem, A., "Pregnancies after intracytoplasmic sperm injection of single spermatozoon into an oocyte", *Lancet*, 340, 17–18 (1992); Craft, I., Bennett, V. and Nicholson, N. (1993), "Fertilising ability of testicular spermatozoa", *Lancet*, 342, 864 (1992); Schoysman, R., Vanderzwalmen, P., Segal-Bertin, G., and van de Casseye, M., "Successful fertilization by testicular spermatozoa in an in-vitro fertilization programme", *Hum.Reprod.*, 8, 1339–1340 (1993); Silber, S. J., Nagy, Z., Liu, J., Tournaye, H., Lissens, W., Ferec, C., Liebaers, I., Devroey P. and Van Steirteghem, A. C., "The use of epididymal and testicular spermatzoa for intracytoplasmic sperm injection: the genetic implications for male infertility", *Hum. Reprod.*, 10, 2031–2043 (1995b); Devroey, P., Liu, J., Nagy, Z., Goossens, A., Tournaye, H., Camus, H. and Van Steirteghem, A., "Pregnancies after testicular sperm extraction and intra-cytoplasmic sperm injection in non-obstructive azoospermia", *Hum. Reprod.*, 10, 1457–1460 (1995). This can even include men with arrested spermiogenesis, since it is evident that spermatids contain all necessary elements for decondensation and complete participation at syngamy. Fishel, S., Aslam, I. And Tesarik, J., "Spermatid conception: a stage too early, or a time too soon?", *Hum. Reprod.* 11, 1371–1376 (1996).; Palermo, G., Munné, S. and Cohen, J., "The human zygote inherits its mitotic potential from the male gamete", *Hum. Reprod.*, 9, 1220–1225 (1994).

In the near future even less mature diploid stages such as secondary spermatocytes and possibly spermatogonia may be used for fertilization or zygote reconstitution; this seems an obvious development, since in some men, spermatogenesis arrests early during meiosis. The in-vitro culture of spermatogonia appears to be hypothetically solved, but clinical application faces major physiological hurdles involving combinations of experimental molecular and cellular strategies that have not yet been developed.

Technical, physiological and genetic problems have already occurred in the new field of single mature gamete manipulation. The presence of Y-deletions in some azoospermic men and possible consequences in male offspring, has recently caused a review and change in regulations by The Dutch Health Council (1996). Health Council of the Netherlands (1996) Committee on in vitro fertilization, "Assisted fertilization: ICSI", The Hague. Publication no. 1996/06E. See also, Cummins, J. M. and Jequier, A. M., "Concerns and recommendations for intracytoplasmic sperm injection (ISCI) treatment", *Hum. Reprod.*, 10 Suppl1: 138–143 (1995).

Another important problem concerns the possible negative consequences certain diagnostic and therapeutic extraction procedures may have on testicular function. Jarow, J., "Intratesticular arterial anatomy", *J.Androl.*, 11, 255–259 (1990); Schlegel, P., "Physiologic consequences of TESE, *Hum.Reprod.*, 11, abstract 159 (1996). Repeated surgical procedures are not only costly and invasive, but in the case of testicular sperm extraction (TESE), can cause transient and even permanent adverse physiologic effects. Schlegel, P., "Physiologic consequences of TESE", *Hum.Reprod.*, 11, abstract 159 (1996). Repetition of these procedures can, in some cases, be avoided by cryopreservation of spermatozoa, but is only possible when sufficient numbers of functional cells are isolated. Silber, S. J., Van Steirteghem, A. C., Liu, J., Nagy, Z., Tournaye, H. and Devroey, P., "High fertilization and pregnancy rate after intracytoplasmic sperm injection with spermatozoa from testicle biopsy", *Hum. Reprod.*, 10, 148–152 (1995a). Although there are anecdotal reports, Patrizio, P., Ord, T., Balmaceda, J. P. and Asch, R. H., "Successful fertilization, pregnancy, and birth using epididymal sperm frozen 24 hours after conventional oocyte insemination", *Fertil. Steril.*, 64, 863–865 (1995); Podsiadly, B. T., Woolcott, R. J., Stanger, J. D. and Stevenson, K., "Case report: pregnancy resulting from intracytoplasmic sperm injection of cryopreserved spermatozoa recovered from testicular biopsy", *Hum. Reprod.*, 11, 1306–1308 (1996), describing sperm survival and birth after cryopreservation of sperm-rich epididymal and testicular aspirations, conventional sperm freezing cannot work for limited numbers of sperm cells. Hewitt J, Cohen J, Mathew T and Rowland G F, "Cryopreservation of semen in patients with malignant disease: role of in vitro fertilization", *Lancet*, 2, 445–446 (1985). Yet it is crucial that a sperm freezing method be developed to avoid repeated surgical attempts at sperm extraction.

Therefore, in cases of very low sperm recovery from azospermic men, a method is needed for preservation and recovery of the sperm so that the necessary surgical procedures are not unnecessarily performed.

In addition, the problems of preserving and recovering single cells or very small biological samples occur in other fields, both scientific and medical. As a single cell is isolated, such as a hematopoetic stem cell, for use in autotransplantation into a patient, the number of cells isolated may be small. Since the procedure typically calls for a period of chemotherapy and/or radiation therapy, the stored cells must be preserved, for example frozen, for autotransplantation after therapy has completed.

Other fields of science and industry also require the isolation and preservation of single cell samples, or small groups of cells.

It is known to use empty zona pellucidae for the culturing of embryos from different species. In these known methods, a relatively large aperture, e.g., spanning about 280°, forms a flap in the wall of the zona through which a micropipette can be used insert embryonic material. In order to retain the embryonic material in the zona, and prevent attack by immune cells after insertion into the oviduct of a host animal, the zona is encased in an agar chip. Willadsen, S. M. "Nuclear Transplantation in Sheep", *Nature,* 320:63 (1986). Empty zona pellucidae have also been used for the storage of embryonic material for laboratory tests.

The zona pellucida is an extracellular coat that is synthesized by the oocyte and surrounds the egg and early embryo of all mammalian species. P. M. Wassarman: "Zona pellucida glycoproteins", *Ann Rev Biochem* 57, 414–442 (1988). The zona pellucida is normally the site of the initial interaction of the spermatozoa with the oocyte. This interaction includes the species-specific spermatozoa-zona pellucida binding and induction of the acrosome reaction (AR), both of which are prerequisites for successful in-vivo fertilization.

Results of cDNA cloning of the zona pellucida genes and analysis of the composition of zona pellucida from several different species indicate that zona pellucida is constituted of three or four sulfated glycoproteins. O. Epifano & J. Dean, "Biology and structure of the zona pellucida: a target for immunocontraception", *Reprod Fertil Dev* 6, 319–330 (1994). The zona pellucida of the mouse oocyte, one of the best studied zona pellucida, is composed of three sulphated glycoproteins termed ZP1, ZP2 and ZP3. P. M. Wassarman, "Zona pellucida glycoproteins", *Ann Rev Biochem* 57, 414–442 (1988); P. M. Wassarman, "Profile of a mammalian sperm receptor", *Development* 198, 1–17 (1990). ZP1 is a homodimer (Mr=185–200 kDa) and its chains are connected by intermolecular disulphide bonds. ZP2 (Mr=120–140 kDa) and ZP3 (Mr=83 kDa) form a heterodimer of long filaments with a repeating structure. P. M. Wassarman, "Zona pellucida glycoproteins", *Ann Rev Biochem* 57, 414–442 (1988); P. M. Wassarman, "Profile of a mammalian sperm receptor", *Development* 198, 1–17 (1990). ZP1 provides a structural integrity for the zona pellucida by cross-linking the ZP2/ZP3 filaments. Only ZP2 and ZP3 have been shown to possess biological functions. The mouse ZP1 is a 623 amino acid polypeptide chain with a signal peptide and a carboxyl terminal transmembrane domain, which is typical of all zona proteins. Epifano, O., et al., *Development,* 121.07:1947–1956.

ZP3 mediates the initial binding of acrosome-intact spermatozoa to the zona pellucida via O-linked side chains. H. M. Florman & P. M. Wassarman, "O-Linked oligosaccharides of mouse egg ZP3 account for its sperm receptor activity", *Cell* 41, 313–324 (1985); T. K. Rosiere & P. M. Wassarman, "Identification of a region mouse zona pellucida glycoprotein mZP3 that possesses sperm receptor activity", *Dev Biol* 154, 309–317 (1992). Following sperm binding, ZP3 induces the AR in the bound spermatozoa. J. D. Bleil & P. M. Wassarman, "Sperm-egg interactions in the mouse: sequence of events and induction of the acrosome reaction by a zona pellucida glycoprotein", *Dev Biol* 95, 317–324 (1983). The acrosome-reacted spermatozoa, which can no longer interact with ZP3, bind to ZP2 and penetrate through the zona pellucida. J. D. Bleil, J. M. Greve & P. M. Wassarman, "Identification of a secondary sperm receptor in the mouse egg zona pellucida: role for maintenance of binding of acrosome reacted sperm to eggs", *Dev Biol* 128, 376–385 (1988). After fertilization, there are molecular changes in ZP2 and ZP3 that constitute a block to polyspermy. ZP3 is converted to a form called $ZP3_f$, which no longer binds acrosome-intact spermatozoa and is incapable to induce the AR. J. D. Bleil & P. M. Wassarman, "Sperm-egg interactions in the mouse: sequence of events and induction of the acrosome reaction by a zona pellucida glycoprotein", *Dev Biol* 95, 317–324 (1983). Since O-linked carbohydrates are implicated in interaction of ZP3 with spermatozoa, and there is no apparent change in the electrophoretic mobility of $ZP3_f$, J. D. Bleil & P. M. Wassarman, "Sperm-egg interactions in the mouse: sequence of events and induction of the acrosome reaction by a zona pellucida glycoprotein", *Dev Biol* 95, 317–324 (1983); J. D. Bleil & P. M. Wassarman, "Mammalian sperm-egg interaction: Identification of a glycoprotein in mouse egg zonae pellucidae possessing receptor activity for sperm", *Cell* 20, 873–882 (1980), this change in ZP3 is thought to be caused by a cortical granule-released glycosidase. D. J. Miller, X. Gong, G. Decker & B. D. Shur, "Egg cortical granule N-acetylglucosaminidase is required for the mouse zona block to polyspermry", *J Cell Biol* 123, 1431–1440 (1993). ZP2 is converted to a form called $ZP2_f$ that no longer interacts with acrosome-reacted spermatozoa. J. D. Bleil & P. M. Wassarman, "Autoradiographic visualization of the mouse egg's sperm receptor bound to sperm", *J Cell Biol* 102, 1393–1371 (1986). ZP2 is cleaved by a protease from the cortical granules, C. C. Moller & P. M. Wassarman, "Characterization of a proteinase that cleaves zona pellucida glycoprotein ZP2 following activation of mouse eggs", *Dev Biol* 132, 103–112 (1989), and is detected by a shift in its electrophoretic mobility (from Mr=120 kDa to Mr=90 kDa) under reducing conditions. J. D. Bleil, C. E. Beoll & P. M. Wassarman, "Mammalian sperm-egg interaction: fertilization of mouse eggs triggers modification of the major zona pellucide glycoprotein, ZP2", *Dev Biol* 86, 189–197 (1981).

There are also reports regarding the composition of the human zona pellucida. S. Bercegeay, M. Jean, H. Lucas & P. Barriere, "Composition of human zona pellucida as revealed by SDS-PAGE after silver staining", *Mol Reprod Dev* 41, 355–359 (1995); J. Moos, D. Faundes, G. S. Kopf & R. M. Schultz, "Composition of the human zona pellucida and modifications following fertilization", *Hum Reprod* 10, 2467–2471 (1995); R. K. Naz & K. Ahmad, "Molecular identities of human sperm proteins that bind human zona pellucida: nature of sperm-zona interaction, tyrosine kinase activity, and involvement of FA-1", *Mol Reprod Dev* 39, 397–408 (1994); R. B. Shabanowitz & M. G. O'Rand, "Characterization of the human zona pellucida from fertilized and unfertilized eggs", *J Reprod Fert* 82, 151–161 (1988); R. B. Shabanowitz, "Mouse antibodies to human zona pellucida: evidence that human ZP3 is strongly immunogenic and contains two distinct isomer chains", *Biol Reprod* 43, 260–270 (1990). Shabanowitz and colleagues reported only two components (Mr=90–110 kDa and Mr=57–73 kDa) under nonreducing conditions and three components (Mr=90–110 kDa, Mr=65–78 kDa, and Mr=57–73 kDa) under reducing conditions. R. B. Shabanowitz & M. G. O'Rand, "Characterization of the human zona pellucida from fertilized and unfertilized eggs", *J Reprod Fert* 82, 151–161 (1988); R. B. Shabanowitz, "Mouse antibodies to human zona pellucida: evidence that human ZP3 is strongly immunogenic and contains two distinct isomer chains", *Biol Reprod* 43, 260–270 (1990). They termed these proteins ZP1, ZP2 and ZP3, respectively. A zona pellucida component corresponding to the mouse ZP1 (Mr=200 kDa) was not detected. Similarly, under reducing conditions Bercegeay et al. found protein components of 80–92 kDa, 58–66 kDa, and 54–72 kDa. S.

Bercegeay, M. Jean, H. Lucas & P. Barriere, "Composition of human zona pellucida as revealed by SDS-PAGE after silver staining", *Mol Reprod Dev* 41, 355–359 (1995). These components likely correspond to mouse ZP2 and ZP3, respectively, based on their molecular weights. Naz and Ahmad showed that the human zona pellucida analyzed under non-reducing conditions exhibited 3 major protein bands of 220, 110 and 55 kDa. The zona pellucida protein that reacted strongest with the sperm proteins was the 55 kDa molecular region (ZP3). R. K. Naz & K. Ahmad, "Molecular identities of human sperm proteins that bind human zona pellucida: nature of sperm-zona interaction, tyrosine kinase activity, and involvement of FA-1", *Mol Reprod Dev* 39, 397–408 (1994). Recently, Moos et al., using a non-radioactive biotinylation- and a lectin-based detection system, found that, under non-reducing conditions, the human zona pellucida of unfertilized eggs is composed of three glycoprotein species designated as ZP1 (Mr~150 kDa), ZP2 (Mr~100 kDa) and ZP3 (Mr~55–65 kDa). J. Moos, D. Faundes, G. S. Kopf & R. M. Schultz, "Composition of the human zona pellucida and modifications following fertilization", *Hum Reprod* 10, 2467–2471 (1995).

In all the above studies, ZP1 was not detected after fertilization. In contrast, in the mouse, ZP1 is present and is apparently unaltered following fertilization. J. D. Bleil, C. E. Beoll & P. M. Wassarman, "Mammalian sperm-egg interaction: fertilization of mouse eggs triggers modification of the major zona pellucide glycoprotein, ZP2", *Dev Biol* 86, 189–197 (1981). Therefore, it has been suggested that in humans, the cortical granule-derived proteases may degrade ZP1 to forms that are not detectable by the electrophoresis process used in the studies. J. Moos, D. Faundes, G. S. Kopf & R. M. Schultz, "Composition of the human zona pellucida and modifications following fertilization", *Hum Reprod* 10, 2467–2471 (1995). See, Morales, P. and Llanos, M., "Interaction of human spermatozoa with the zona pellucida of oocyte: development of the acrosome reaction", Frontiers in *Bioscience*, 1, d146–160 (Aug. 1, 1995).

An artifical zona pellucida is disclosed in U.S. Pat. No. 5,272,086. This artificial zona is formed of a crosslinked microporous hydrogel, for implantation of a blastomere in the uterus of an animal species different from the blastomere species. In addition, purified zona pellucida proteins or glycoproteins are known. See, U.S. Pat. Nos. 4,801,689, and 4,847,363.

SUMMARY OF THE INVENTION

The present invention provides an empty zona pellucida of an animal, especially a mammal or a human, a method of making an empty zona pellucida, a method of using an empty zona pellucida for the isolation and preservation of small or sparse cellular biological samples, such as single cells, and a zona pellucida devoid of oocyte or embryonic contents, and having another cell placed therein.

In particular, the present invention relates to a new approach to spermatozoa cryopreservation, which allows freezing and recovery of single sperm cells. This procedure can be applied even in the most extreme cases, such as those men who have less than 100 sperm cells aggregated in the final suspension used for an ICSI attempt. The issue of losing sperm through conventional addition and removal of cryoprotectant in relatively large volumes of media and sperm preparation methods is circumvented by insertion of the sperm cell into an enclosed porous capsule, which can be properly visualized and handled microscopically before and after cryopreservation. The chosen vehicle for this purpose is the zona pellucida from which oocyte or embryonic cellular material has been removed. The feasibility was demonstrated by inserting small groups of spermatozoa and even single cells into evacuated empty rodent and human zonae for cryopreservation; followed by thawing, recovery and fertilization with high efficiency.

The zona pellucida has a number of advantageous characteristics, which include a size of about 100 $\mu$m, a relatively tough wall, biocompatibility with cells and hosts, freeze and thaw durability, and availability. The zona pellucida, when separated from the oocyte or embryonic contents, provides a microenvironment which allows isolation and retention of most cells types, including sperm, therein. Since the zona pellucida is relatively large, it is easily handled and its location readily determined. However, the size is small enough to ensure that the cells are not lost within the space within the zona pellucida, and to ensure that thermal capacitance is small, allowing effective external temperature.

Therefore, the present invention provides a biocompatible capsule for storing non-native cells therein having a size of between about 25–300 $\mu$m. This capsule may be an empty zona pellucida or synthetic zona pellucida, or be formed of other materials, including proteins, glycoproteins, carbohydrates, synthetic or semisynthetic polymers, and/or copolymers or block copolymers. Preferably, the capsule has an inner chamber which is spherical or ellipsoidal having a diameter of about 20–250 $\mu$m.

When a zona pellucida is employed, the glycoproteins therein may be reacted with sperm acrosome in order to transform the zona pellucida. This is especially the case where the sperm to be stored in the zona pellucida are capable of themselves transforming the zona pellucida, for example being from the same species.

Preferably, the zona is processed to remove not only the cellular oocyte or embryonic contents, but also antigens other than those intrinsic to the zona pellucida itself. This processing includes removal of oocyte or embryonic contents, washing, and possibly enzymatic treatments.

According to one embodiment of the invention, the zona pellucida is preferably from a different species than the cell stored therein, for example a human sperm stored in a hamster zona pellucida. This tends to limit biological reactions between the sperm and zona pellucida.

Further, the preferred zona pellucida are large and easily isolated, and therefore may be easily recovered after a freeze thaw cycle, as compared to a naked normal cell. The zona pellucida need not be prepared individually for each procedure, and may therefore may be packaged and shipped, for example frozen or freeze dried. For example, one or more prepared empty zona pellucida may be provided in a physiological solution in a capillary tube, ready for use as needed.

The zona pellucida is prepared as follows. The Corona radiata, which includes cumulus corona cells, adherent to the exterior of the zona pellucida, is removed by known methods, which may include mechanical removal and treatment with hyaluronidase. The zona pellucida is held in place with a suction micropipette, having a diameter of, for example, 40–50 $\mu$m. The incision or aperture is made in the wall by a sharp instrument which "files" away a small portion of the wall. According to some embodiments, a micropipette is inserted and the oocyte contents slowly withdrawn. This micropipette may be, for example, a 5–10 $\mu$m diameter sharpened glass micropipette. According to one option, two apertures are formed in the wall of the zona, allowing extra-zona medium to equalize the internal pressure while the contents are being withdrawn. If the zona pellucida begins to collapse, a solution may be injected into the inner space to reinflate it. After all of the oocyte cytoplasm is removed, the zona pelludica may be washed or flushed, and is then stored in a capillary tube for later use. According to other embodiment, the cellular contents of the zona pellucida are removed by a positive internal pressure assured by injection of medium through a micropipette inserted through the wall of the zona. As medium is injected, the cellular material is flushed through the aperture, adjacent to the micropipette, to the external space.

A number of alternatives thus exist to the formation of the pressure relief aperture in the zona pellucida. A single aperture may be formed, though which the cellular material in the zona pellucida, which may be a fertilized or unfertilized oocyte, is withdrawn. The micropipette may then be withdrawn from the zona, and fresh medium drawn into the micropipette. The micropipette is then reinserted through the aperture, and the medium in the micropipette used to equalize the internal pressure, so that the zona pellucida is spherical. Alternately, medium may be expelled into the zona pellucida by a micropipette without first withdrawing the oocyte or embryo therewithin. The pressure forces the cellular material in the zona pellucida to be expelled through the aperture, adjacent to the micropipette. The medium in the micropipette may be used to wash the zona, assuring that all of the cellular material is expelled.

The optional pressure relief hole may also be made by a laser, such as a 1.48 $\mu$m diode laser, according to known techniques. Rink K., Delacrétaz G., Salathé R. P., Senn A., Nocera D. and Germond M., "1.48 micron Diode Laser Microdissection of the Zona Pellucida of Mouse Zygotes" Laser-Tissue Interaction V, *Proc. SPIE* 2134A, 412–422 (1994); Germond M., Nocera D., Senn A., Rink K., Delacrétaz G. and Fakan S., "Microdissection of mouse and human zona pellucida using a 1.48 micron diode laser beam: Efficacy and safety of the procedure", *Fertil. Steril.*, in print (1995); Rink K., Delacrétaz G., Salathé R. P., Senn A., Nocera D., Germond M. and Fakan S., "Non-contact Microdrilling of Mouse Zona Pellucida with an Objective-Delivered 1.48 micron Diode Laser" *Lasers Surg Med.*, submitted (1994); Germond M., et al., "Improved fertilization and implantation rates after non-touch zona pellucida microdrilling of mouse oocytes with a 1.48 $\mu$m diode laser beam", *Hum. Reprod,* 11(5):1043–1048 (1996).

The empty zona pellucida is then used to store a single cell or small number of cells, for example, for cryopreservation. In this case a single cell, for example a sperm, is placed in a micropipette, and inserted into the interior of the empty zona pellucida. Since a sperm is about 1 $\mu$m diameter (with a longer tail), a large number may potentially be stored within a single zona pellucida. Preferably, only a small number are inserted, for example less than 100 sperm, more particularly about 1–20 sperm. The zona pellucida and its contents may then be subjected to various treatments, such as cryopreservation. Preferably, the zona pellucida and its contents are placed in a capillary tube, with air bubbles as lateral barriers, so that the zona pellucida may be later identified for use. Multiple zona pellucidae may be stored in the same capillary tube.

After the cells are placed in the zona pellucida, stored, and the zona pellucida isolated, the cell may then be removed from the zona pellucida for use. In this case, a micropipette is inserted through the wall of the zona pellucida, in proximity to a cell, under microscopic guidance. The cell is withdrawn into the micropipette, with care taken to avoid collapsing the zona pellucida by withdrawing too much fluid too fast.

The cell may then be directly deposited in a desired location. For example, if the cell is a sperm, it may be directly deposited in an oocyte to be fertilized by a known intra-cytoplasmic sperm injection (ICSI) process. Other procedures may also be used for fertilization of an egg with a sperm, and indeed the use of the zona pellucida storage system is not limited to in vitro fertilization techniques.

Preferably, all the components necessary for storing cells in a zona pellucida are available in a kit of parts, for example for the cryopreservation of single sperm or sperm precursor cells. In this case, the micropipette(s), solutions, reagents and cryopreservation solution are provided. Further, a separate but related kit may also be provided for thawing the zona pellucida and intra-cytoplasmic sperm injection (ICSI) procedure, or other in vitro fertilization procedure. These kit may be provided together, but preferably are provided in separate sterile containers, due to the different times and conditions of use.

In some cases, it may be advantageous to tag the zona pellucida for increased ease of isolation. In this case, the zona pellucida may be tagged with beads or particles, for example magnetite particles or latex beads, which may be identified visually or otherwise. While dyes may also be used to tag the zona, these typically are both cytotoxic and may interfere with visualization.

The present invention thus provides a method for tagging microcapsules by the insertion of a composition or mixture, which may be visibly or automatically determined, and which may optionally be used to distinguish different microcapsules, e.g., zona pellucidae. For example, with three different taggants, seven different zona may be distinguished, assuming only the presence or absence of a particular taggant is detected. With differing concentrations measured, for example trilevel tagging, the number of zonae which may be distinguished rises to 31. The tag may be determined through an optical microscope or specially designed detector which, for example, assesses zona pellucidae within a capillary tube.

As stated above, the zona pellucida may be constructed artificially or synthetically, so long as it meets the required characteristics thereof. Therefore, the zona pellucida used to store the cells need not be derived from an animal. This possibility provides the additional advantage of reducing an antigen load during use of the cells stored in the capsule.

The addition of DTT is considered advantageous for the freezing protocol, and it may be used in conjunction with the method according to the present invention. Sawetawan, C., Bruns, E. S. and Gail, S. P., "Improvement of post-thaw motility in poor quality human semen", *Fertil. Steril.*, 60, 706–710 (1993), or small amounts of TEST-yolk or other freezing buffers. Also, the human zonae can be pre-treated in order to avoid sperm-ZP3 binding, and consequently the acrosome reaction and motility reduction. Pre-treating animal zonae is likely unnecessary, but certain enzyme inhibitors might be used to avoid non-specific interaction between molecules released from lysed ova and other spermatozoa.

Other objects and advantages of the present invention will become apparent from a review of the figures and detailed description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The preferred embodiments of the invention will be explained by reference to the drawings, in which.

DETAILED DESCRIPTION OF THE PREFERRED EMBODIMENTS

Figure 1:
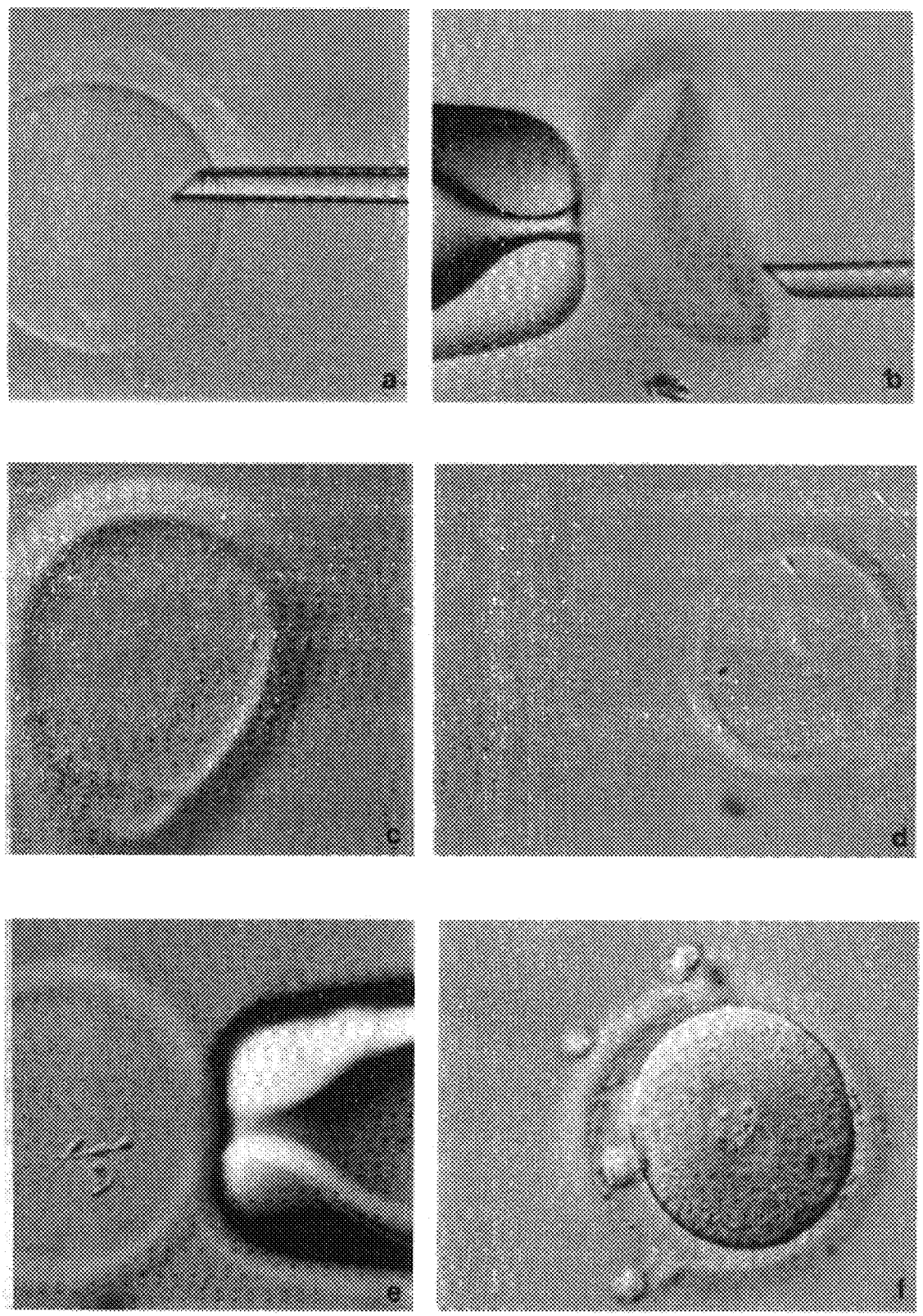
FIG. 1a shows a pre-fertilization human zona pellucida with two small incisions of which one is visible (arrow). The oocyte and polar body were removed using an extraction micro-tool inserted through one of the incisions. The extraction micro-tool had a sharp bevel and a diameter of 15 μm.
FIG. 1b shows the effect of excessive suction may collapse the zona pellucida, which can be re-inflated by inserting small amounts of medium after passing the needle through the hole (arrow). Alternatively, a few minute wait will allow the zona will fill up spontaneously and recover its original shape.
FIG. 1c shows a human post-fertilization zona from an ICSI patient from which the abnormal embryo was removed. Only one sperm cell is inserted and located at 3 o'clock.
FIG. 1d shows a mouse zona pellucida with two human sperm cells inside at same magnification as FIG. 1c.
FIG. 1e shows an aggregation of motile spermatozoa after thawing of a mouse zona pellucida. Focus is on five human sperm cells, all of which could be isolated with an ICSI-needle and prepared for ICSI. Aggregation occurs typically after injection of more than three sperm cells into the zona pellucida and inhibits motility.
FIG. 1f shows a normally fertilized in vitro matured spare human oocyte, injected with a sperm cell frozen and thawed singly in an empty hamster zona pellucida.

Materials and methods
Equipment, culture media and tools

All micromanipulation was performed in HEPES buffered human serum albumin-substituted Human Tubal Fluid. Cohen, J., Malter, H., Grifo, J. and Talansky, B., *Micromanipulation of human gametes,* Raven Press, New York (1992).

Micromanipulation was performed in shallow Falcon 1006 dishes using eight, 5 μL droplets surrounding a 5 μL droplet containing PVP. Palermo, G., Joris, H., Devroey, P., and Van Steirteghem, A., "Pregnancies after intracytoplasmic sperm injection of single spermatozoon into an oocyte", *Lancet,* 340, 17–18 (1992). Two different solutions of PVP were used: (I) a 10% solution for sperm capture and insertion in empty zonae (Medi-Cult, Danmark), (II) a 12% solution for sperm recovery from the thawed zonae. The ICSI procedures were performed at 37° C., but all other micromanipulation was performed at room temperature in order to reduce sperm velocity. The procedures were performed at 40× using an IX-70 inverted Olympus microscope equipped with Hoffman interference optics and connected to a 14-inch monitor. The microtools for PZD, ICSI and zona drilling were fabricated according to known techniques, as described in Cohen, J., Malter, H., Grifo, J. and Talansky, B., *Micromanipulation of human gametes,* Raven Press, New York (1992); Palermo, G., Joris, H., Devroey, P., and Van Steirteghem, A., "Pregnancies after intracytoplasmic sperm injection of single spermatozoon into an oocyte", *Lancet,* 340, 17–18 (1992); Palermo G D, Cohen J, Alikani M, Adler A, and Rosenwaks, Z., "Intracytoplasmic sperm injection: a novel treatment for all forms of male factor infertility", *Fertil. Steril.,* 63, 1231–1240 (1995).

A new tool was developed especially for extraction of cellular material from the zonae. This tool was pulled from Drummond glass using pulling parameters generally applied to ICSI needles. It was cut on a microforge to have a 15 μm diameter tip and beveled at a 45° angle without a spike.

Eggs were incubated after ICSI using standard procedures described elsewhere. Cohen, J., Malter, H., Grifo, J. and Talansky, B., Micromanipulation of human gametes, Raven Press, New York (1992); Palermo G D, Cohen J, Alikani M, Adler A, and Rosenwaks, Z., "Intracytoplasmic sperm injection: a novel treatment for all forms of male factor infertility", *Fertil. Steril.,* 63, 1231–1240 (1995). Data comparisons were made using chi-square analysis or Fisher's exact test when applicable.

Source of gametes and embryos

All protocols were approved in 1995 by the Internal Review Board of Saint Barnabas Medical Center, Livingston, N.J. Forty-nine patients undergoing egg retrieval, IVF and ICSI consented to donate unused gametes and embryos (discarded biological material). Six ICSI patients were used for cryopreservation of individual sperm cells. Empty zonae were obtained from seven patients, and 21 other patients consented to donate unfertilized and immature eggs. Fifteen fertile men consented to have their sperm cells used for controls.

Source and preparation of spermatozoa

Six ICSI patients had severe oligo-astheno-teratozoospermia. Their spermatozoa were used for six cryopreservation experiments. The volumes of their final sperm suspensions (less than 50 μL) and counts would have normally been too low or considered borderline for conventional sperm suspension cryopreservation. Spermatozoa were isolated by centrifugation at 1800 g and mini-percoll as described elsewhere. Ord, T., Patrizio, P., Marcello, E., Balmaceda, J. P. and Asch, R. H., "Mini-percoll: a new method of semen preparation for IVF in severe male factor infertility", *Hum. Reprod.,* 5, 987–989 (1990); Palermo G D, Cohen J, Alikani M, Adler A, and Rosenwaks, Z., "Intracytoplasmic sperm injection: a novel treatment for all forms of male factor infertility", *Fertil. Steril.,* 63, 1231–1240 (1995). The sperm suspensions were incubated at 37° C. in 5% $CO_2$ in air prior to sperm cell isolation and insertion into empty zonae pellucidae for cryopreservation. Individual sperm cells were then successfully frozen and thawed in empty zonae.

Sperm from men with normal semen analysis was used for testing the fertilizing ability of donated research oocytes by ICSI. These spermatozoa were not cryopreserved and served as controls for thawed sperm from infertile men. The control sperm samples were obtained from 15 consenting patients who needed in-vitro fertilization (IVF) for female factor related infertility. These fertile samples were not frozen in order to provide a maximum rate of fertilization with ICSI using donated spare oocytes, and compare with rates of individually thawed sperm from infertile men recovered from empty zonae.

Source and preparation of empty zonae pellucidae

Empty zonae were obtained from multiple sources:

(I) pre-fertilization human zonae from immature eggs;

(II) post-fertilization sperm-free human zonae from ICSI embryos, with abnormal fertilization or development; and (III) pre-fertilization mouse zonae and, (IV) pre-fertilization thawed hamster zonae.

Pre-fertilization zonae were obtained from immature human oocytes from which the cumulus was removed using a hyaluronidase suspension and the corona was stripped using fine micropipettes in preparation for ICSI. Palermo, G., Joris, H., Devroey, P., and Van Steirteghem, A., "Pregnancies after intracytoplasmic sperm injection of single spermatozoon into an oocyte", Lancet, 340, 17–18 (1992). Five consenting patients provided a total of 18 eggs at the GV or M-I stage for this research.

Pilot studies had shown that two small incisions in the zonae improved extraction of the egg ooplasm and insertion of the sperm cells in the evacuated zonae, because this prevented collapse of the zona during suction and excessive inflation when the sperm was inserted, as shown in FIGS. 1a and 1b.

Holes were made chemically in only three pre-fertilization zonae by releasing acidified Tyrode's solution from a 10 μm open microneedle. Holes in all other zonae were made mechanically by partial zona dissection with a spear-shaped closed microneedle.

Cytoplasm was extracted using a beveled 15 μm micropipette, as shown in FIG. 1a, connected in turn to a Narishige IM-6 suction device made with thin glass, and equipped with a wide-bore metal plunger, without the use of O-rings. The zona was positioned so that one of the two incisions was situated at the three o'clock position. The beveled microtool was inserted through the aperture using the sharp edge on the lower end of the bevel. The tool was moved through the oolemma, and the cytoplasm was fully aspirated until the zona was empty. The pipette was occasionally emptied outside the zonae or more medium was sucked up to remove any sticky cytoplasm from the pipette-tip.

Ten post-fertilization zonae were obtained from two consenting ICSI patients, as shown in FIG. 1c. The embryos were either activated, digynically fertilized or abnormal. None were considered suitable for transfer or embryo cryopreservation. Incisions were made mechanically using PZD. Cells were removed using the extraction procedure described above.

Mouse eggs were obtained after flushing from the oviduct using superovulated 10–12 week-old CB6F1 hybrid females. Cumulus and corona cells were removed as described in Levron, J., Willadsen, S., Bertoli, M. and Cohen, J., "The development of mouse zygotes after fusion with synchronous and asynchronous cytoplasm", Hum. Reprod., 11, 1287–1292 (1996). Mechanical PZD was performed to make two incisions. The whole contents of the egg were removed, including the oolemma and polar body, using the extraction procedure described above. During the suction procedure, the zona frequently collapsed. When this occurred, the pipette was partially withdrawn with its beveled aperture facing the zona pellucida and fresh medium was aspirated and gently blown in, to re-inflate the collapsed zona, as shown in FIG. 1b.

Frozen hamster eggs were obtained from Charles River Inc. (Wilmington, Mass., USA). The eggs were frozen in 1.5M propylene glycol and mixed in a sucrose solution during thawing. The straws were thawed for two minutes in air, three minutes at 37° C. in water, two minutes at room temperature and expelled for 10 minutes in HEPES-HTF at room temperature. Thawed intact eggs were washed four times in culture medium and micro-manipulated in a fashion similar to the mouse zona procedure described above. Extraction micropipettes needed changing frequently because of the adhesive nature of the thawed cytoplasm and its response to the extraction process.

Sperm insertion into zonae and cryopreservation

Figure 2:
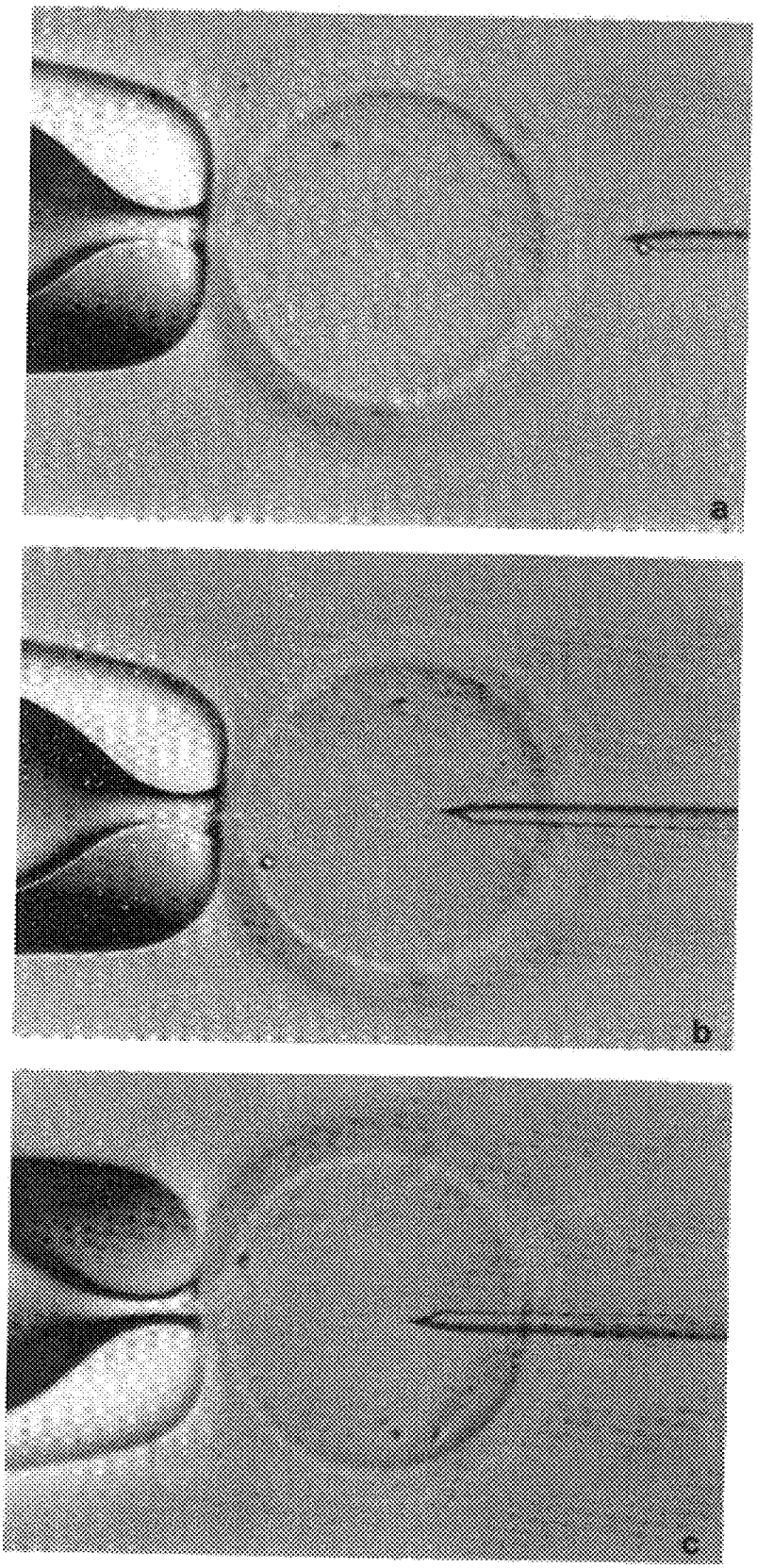
FIG. 2a shows an empty pre-fertilization human zona pellucida. The arrow indicates the side of incision, which runs between 3 and 4 o'clock. The ICSI needle has a small oil bubble at the tip and is filled with two sperm cells in 8% PVP. Note that the oil bubble is at 8 o'clock after expulsion of fluid.
FIG. 2b shows the micro-tool inserted into the zona pellucida, through the incision, with one sperm released slowly and visible at 12 o'clock.
FIG. 2c shows a second sperm cell inserted into the zona pellucida. Both spermatozoa are now between the 12 and 1 o'clock positions. The needle is pre-loaded with 12% PVP for sperm extraction from the thawed zona. Tool insertion after thaw is similar to that shown here.

All spermatozoa were released into the 10% PVP solution prior to insertion into empty zonae. If the concentration and/or motility permitted, they were released by adding 1 μL of the sperm suspension; if not, they were individually taken from small 2–5 μL droplets of sperm suspension using an ICSI microtool. Some spermatozoa in PVP were immobilized mechanically using the ICSI microtool and then injected into eight evacuated human zonae kept in HEPES buffered solution. Motile sperm cells were picked up into PVP medium and inserted into empty human or animal zonae in all other experimental groups, as shown in FIG. 2. All zonae were in HEPES buffered HTF and kept at room temperature. The number of cells inserted into each zona was between 1 and 15, but only three zonae contained more than 5 cells, as shown in FIGS. 1c, 1d and 1e. The individual sperm cells were counted twice and witnessed during and immediately after insertion. Sperm release from the microtool was done slowly in order to minimize inflation of the zona. Between 3 to 15 zonae were treated this way for each experiment. Sperm cells were visualized a third time in order to ensure an exact count prior to cryopreservation. Hamster zonae were injected with single sperm cells.

Injected zonae were moved to an 8% glycerol solution using a phosphate buffered solution (PBI) supplemented with 3% human serum albumin. The zonae were frozen singly in 0.25 mL sterile plastic straws (IMV International, Minneapolis, Minn., USA; #ZA475) between two small air bubbles to indicate their position. One end of the straw was closed using sealant PVA powder, while the other end was heat sealed. The freezing procedure was based on a simple standard semen cryopreservation protocol by exposure to liquid nitrogen vapor for 120 minutes or overnight followed by a plunge into liquid nitrogen. The straws were kept in liquid nitrogen for at least 48 hours. TEST-yolk buffer and other commercially available semen freezing media were not used, as it was suspected that the zonae could be lost or would float on the surface of the viscous solution.

Thawing, sperm recovery and ICSI

Straws containing zonae were thawed in a water bath at 30° C. for 30 seconds. One end of the straw was cut with sterile scissors, into which a 16-gauge needle of a syringe with raised plunger was inserted. The other side was then cut and the medium was expelled as far as the first bubble by gentle depression of the plunger. The straw was inserted into a medium droplet and the cryopreservation medium containing the zona was slowly released until the second bubble was released. The zona was gently washed four times and pipetted into an ICSI dish containing eight droplets of HEPES buffered medium and a central droplet with 12% PVP in supplemented intra-cellular solution.

The zona was positioned using the holding pipette and a PVP-filled ICSI microtool. Spermatozoa were counted and their motility assessed by rotating and rolling the zona in place. Next, the zona was positioned so one of the incisions and a sperm cell were lined up to allow penetration of the ICSI needle and aspiration of the sperm cell (mechanical recovery method). Minimum suction was used for this process. Some sperm cells showed considerable motility within the zona. These cells were aspirated by positioning the needle at the contra-lateral side and applying suction when the sperm cell passed the needle aperture. All sperm cells were removed one by one and released gently in the PVP solution. Any still motile were immobilized using the microneedle.

Chemical methods of sperm removal were also employed. In a first chemical method, an enzymatic digestion of the zona pellucida was employed. The zonae were pipetted into a 0.1% pronase solution. An ICSI microtool was inserted in the partially digested zona mass in which most sperm cells became trapped. Some motile cells escaped from the digested zona. Trapped cells were more difficult to remove.

The second chemical method involved the use of acidified Tyrode's solution for removal of zona material. The reduced pH immobilized sperm cells rapidly, and the digested zona mass trapped the cells, from which spermatozoa could be removed by aggressive pipetting with the ICSI tool.

The mechanical removal methods are preferred to the chemical removal methods, the results of which are discussed below.

Recovered sperm were immediately injected into one-day old MII or in-vitro matured eggs. The sperm was released into the egg with the polar body at either the 7, 8 or 11 o'clock position, since this optimized results in our work using fresh eggs. Blake, M., Garrisi, G. J., Sadowy, S., Reing, A., Tomkin, G., Scott, R. and Cohen, J., "Sperm Head and Spindle Position during Intra-Cytoplasmic Sperm Injection determine Fertilization and Development Outcome", American Society for Reproductive Medicine, abstract O-058 (1996). This is believed to allow close proximity between the injected sperm cell and the metaphase plate. Injected eggs were washed four times in culture medium and incubated in HTF supplemented with human serum. Control eggs were injected with fresh normal motile sperm cells after immobilization in PVP solution. Eggs were checked after 20 hours for the presence of polar bodies and pronuclei using an IX-70 (Olympus) inverted microsocope with 40× and Hoffman interference optics (FIG. 1f). Cleavage into cells after an additional culture period of 20–28 hours was used to confirm these observations.

Results

General findings and considerations

A total of 50 empty zonae were used for these experiments, of which 28 were from human oocytes or embryos; 194 spermatozoa were selected and injected into the empty zonae for freezing (FIG. 2). Only one zona (2%) from a mouse egg, was not found upon thawing; consequently the sperm cells inside it were lost. It is not surprising that it was a mouse and not a hamster or human zona which was lost, since both the latter have a larger mass and do not float as much as mouse zonae do when pipetted. In all but three human zonae, sperm cells were removed by inserting an ICSI micro-tool and applying suction (mechanical method of sperm recovery). Spermatozoa were not lost before freezing through the narrow mechanical PZD incisions in 25 human zonae, but 21% of sperm were lost using acidified Tyrode's solution for zona drilling (p<0.001). See Table I. The number of sperm lost through holes after thawing ranged from 10% to 37% (p<0.05). The highest loss was again found in the zonae in which larger holes had been made. Sperm loss after thawing through narrow incisions happened occasionally because of inadvertent excess suction applied through the holding pipette. This could be avoided by visualizing both holes prior to micromanipulation and sperm recovery. The rate of sperm loss'through the incisions diminished markedly with increased experience.

TABLE I

Individual sperm loss through holes after sperm insertion into evacuated human zonae before and after freezing

| Type of hole (source of zona) | Sperm injected | Number of evacuated zonae | Number of sperm lost/ injected (pre-freeze) | Number of sperm lost/ injected (post-thaw) |
|---|---|---|---|---|
| low pH (egg zona) | motile | 3 | 7/34 (21%)[a,b] | 10/27 (37%)[c,d] |
| mechanical (egg zona) | motile | 4 | 0/20 (0%)[a] | 6/20 (30%)[c] |
| mechanical (embryonic zona) | motile | 10 | 0/30 (0%)[a] | 3/30 (10%)[c,d] |
| mechanical (egg zona) | immobilized | 8 | 0/40 (0%)[a,b] | 6/40 (15%)[c] |

[a]difference between mechanical groups combined and low pH; p < 0.001
[b,d]p < 0.05
[c]difference between mechanical groups combined and low pH; p < 0.05

The number of sperm lost during and after thawing did not vary greatly between the mechanical and chemical recovery methods, as shown in Table II. But, in the three chemically treated zonae, sperm cells often became trapped and immobilized in the remains of the digested glycoprotein matrix. All spermatozoa (8/8) exposed to acidified solution were immobilized without damage, whereas 5/7 exposed to pronase were either partially or completely damaged. At least three heads digested from among the least motile spermatozoa; presumably because of pronase activity on the acrosome reacted cell. All tails which were broken vigorously during immobilization were also digested by the pronase. No sperm damage occurred when recovered by the mechanical method.

Both mechanical preparation of the zona pellucida by partial zona dissection and mechanical sperm insertion and recovery by suction into an ICSI needle are preferred and were used in all further experiments, as shown in FIG. 2.

TABLE II

Loss and damage of individual sperm cells during thawing and recovery into a microneedle and subsequent immobilization in PVP

| Sperm recovery procedure (source of zona) | Number of sperm lost during and after thawing | Number of sperm damaged during and after recovery[a] |
|---|---|---|
| zona digestion by pronase | 3/10 | 5/7 |
| zona digestion by reduced pH | 2/10 | 8/8 |
| mechanical removal through microneedle (egg zona) | 6/20 | 0/14 |
| mechanical removal through microneedle (embryonic zona) | 3/30 | 0/27 |

[a]differences between mechanical and other groups combined; p < 0.005

Motility recovery and general efficiency

The recovery of motility was determined by visualizing sperm cells for at least 10 seconds inside the zona pellucida at 40× immediately following thawing and cryoprotectant removal, but prior to insertion of micro-tools into the culture media droplets. Some spermatozoa inserted into human zonae appeared caught up in cytoplasmic remnants or crevices inside the glycoprotein matrix, but this occurred less frequently when animal zonae were used. Aggregation of spermatozoa also appeared to inhibit individual motility, but was avoided when three or less spermatozoa were inserted. See FIGS. 1c, 1d and 1e. Some cells which were motile, but did not show marked velocity, became progressively more motile after aspiration and exposure to medium. Motility recovery rates were defined as the percentage of motile cells seen, and varied between 65% to 100% (average 82%). See Table III. It is possible that these rates could have been higher, since some motile cells were lost through holes in the zonae.

Fertilizing ability of individually cryopreserved spermatozoa

A total of 103 research oocytes from 21 patients were available for testing the fertilizing ability of the cryopreserved sperm cells using ICSI. The oocytes were randomly allocated to fresh control spermatozoa from fertile men (n=47) and thawed sperm from infertile men (n=56). Consequently, only a small proportion of the recovered sperm cells could be tested due to the shortage of research material. Thirty-seven oocytes were in-vitro matured, and the remainder were mature one-day old cells which had not fertilized after routine ICSI or IVF. The incidences of fertilization of in vitro matured and mature oocytes were 51.3% and 51.5%, respectively.

The fertilization rates for the fresh and freeze-thawed groups were 53.2% and 50.0% respectively. See FIG. 1f. The

TABLE III

Post-thaw motility and sperm recovery of human spermatozoa individually inserted into and mechanically removed from human, mouse and hamster zonae pellucidae

| Type of hole (source of zona) | Zona pellucida species | Sperm condition pre-freeze | Number of evacuated zonae | Individual sperm cells inserted | Motility recovery | Sperm recovery in microneedle after isolation from zona and immobilization in PVP |
|---|---|---|---|---|---|---|
| low pH (egg zona) | human | motile | 3 | 34 | 11/17 (65%) | 15/34[a,b] (44%) |
| mechanical (egg zona) | human | motile | 4 | 20 | 11/14 (79%) | 10/20[c] (50%) |
| mechanical (embryonic zona) | human | motile | 10 | 30 | 24/27 (89%) | 25/30[a,c] (83%) |
| mechanical (egg zona) | human | immobilized | 8 | 40 | not applicable | 34/40[b,c] (85%) |
| mechanical (egg zona) | mouse | motile | 7 | 35 | 22/30 (73%) | 25/30[a,c] (83%) |
| mechanical (frozen egg zona) | hamster | motile | 15 | 15 | 14/14 (100%) | 14/15[b,c] (93%) |

[a] $p < 0.005$
[b] $p < 0.001$
[c] $p < 0.05$

The efficiency of the procedures was determined by attempting to isolate each sperm cell from the thawed zona using a microtool, subsequent deposition into the PVP solution and individual immobilization as is usually performed for ICSI. The sperm recovery rate was calculated as the ratio of isolated and immobilized sperm cells after thawing, compared to initial sperm insertion count prior to freezing. The rates varied from 44% to 93% (average 73%). Rates of recovery over 80% were found in experiments involving rodent zonae and human zonae which were embryonic in origin or in which the spermatozoa were immobilized prior to freezing. Significantly ($p<0.05$) lower rates (50%) were found in pre-fertilization human zonae, but this could have been caused by incomplete removal of the egg contents in one of the experiments. The use of only one to three sperm cells per zona pellucida appeared optimal.

While it is preferred to place less than three sperm cells in a zona, in one case, the potential of this cryopreservation method was shown by inserting single sperm cells into 15 empty hamster zonae, from which all but one of the sperm cells were recovered.

difference was not significant. Both rates were, however, significantly lower ($p<0.001$) than the routine incidence of fertilization in the ICSI program of one of the inventors hereof, in 98 patients treated during the same study period of three months: 1078/1376 (78.3%), indicating the inferior quality of in-vitro matured and aged one-day old oocytes compared to fresh metaphase-II oocytes. Obvious differences in fertilization rates were not found when different experiments were compared, as shown in Table IV. Although sperm cells recovered from chemically digested zonae were able to fertilize (3/12), two of the fertilizing sperm cells were already damaged when injected and did not have intact tails. It should also be noted that only 3/10 eggs fertilized, after injection of sperm cells, which were immobilized prior to freezing. The formation of the pronuclei in these eggs appeared delayed, but this observation may be biased because of the tiny sample size. More human sperm cells frozen in animal zonae fertilized oocytes (14/18 [78%]) after recovery than sperm cells frozen in human zonae (14/38 [37%]), but the significance level was low ($p<0.05$).

TABLE IV

Fertilization by ICSI using one day-old unfertilized MII or in vitro matured human eggs of human sperm cells individually frozen in evacuated human, mouse and hamster zonae pellucidae

| Sperm recovery procedure (source of zona) | Zona pellucida species[a] | Sperm condition pre-freeze | Number of human eggs injected with thawed sperm | Number of eggs fertilized[a] | Number of control eggs injected with fresh sperm | Number of eggs fertilized |
|---|---|---|---|---|---|---|
| chemical (egg zona) | human | motile | 12 | 3 | 9 | 4 |
| mechanical (egg zona) | human | motile | 16 | 8 | 8 | 5 |
| mechanical (egg zona) | human | immobilized | 10 | 3 | 9 | 4 |
| mechanical (egg zona) | mouse | motile | 10 | 7 | 12 | 6 |
| mechanical (frozen egg zona) | hamster | motile | 8 | 7 | 9 | 6 |
| Total | | | 56 | 28 (50.0%) | 47 | 25 (53.2%) |

[a] $p < 0.05$ when comparing fertilization rates between all human sperm frozen in human zonae with those frozen in animal zonae.

Discussion

The results show that freezing and efficient post-thaw recovery of a single or a few spermatozoa is possible according to the present invention, via injection into evacuated empty human or animal zonae pellucidae. Sperm cells were inserted into empty zonae rather than into the perivitelline space of intact eggs or embryos, since oolemma and blastomere membranes lysed using the typical sperm freezing protocols. Complex cryoprotectants typically used for sperm freezing such as TEST-yolk buffer were not used because empty zonae have a tendency to float in viscous solutions. Similarly, the zonae were not placed in PVP-solution for sperm pick-up after thawing, since this often collapsed the entire matrix structure, making sperm removal very difficult.

The preferred method according to the present invention does not use any enzyme, enzyme inhibitor or motility enhancer, and is entirely based on combinations of physical micromanipulation procedures, the general practice of placing embryos allocated to cryopreservation in straws, and the physics of standard semen cryoprotection.

Twelve percent PVP is preferred over 8–10% since it provided gentle and controlled pick-up of thawed spermatozoa. Zonae with two pre-drilled gaps were preferred, since they permit simultaneous release and absorption of fluids, other than those exchanged by the ICSI and extraction needles. Single spermatozoa frozen according to the present invention are not lost in the vial or supernatant and do not adhere to debris, plastic or glassware.

It was shown here that more than three-quarters of sperm injected and frozen in empty rodent zonae can be recovered for ICSI and are able to fertilize. In the most extreme demonstration of this method, the ratio of zonae to sperm cells was one-to-one. The high recovery rate with animal zonae is probably because of the reduced chance of sperm binding to zona receptors.

Although the present results were obtained with spermatozoa from men with extreme oligospermia, average motility recovery rates are considerably higher than those generally reported for moderately abnormal semen and comparable to results of donor semen or moderately oligospermic patients treated with a combination of Cryoseeds and dithiothreitol (DTT). Bongso, A., Jarina, A. K., Ho, J., Ng, S.C. and Ratnam, S. S., "Comparative evaluation of three sperm-washing methods to improve sperm concentration and motility in frozen-thawed oligozoospermic and normozoospermic samples", Arch. Androl., 31, 223–230 (1993); Verheyen, G. Pletincx, I. and Van Steirteghem, A., "Effect of freezing method, thawing temperature and post-thaw dilution/washing on motility (CASA) and morphology characteristics of high quality human sperm", Hum. Reprod., 8, 1678–1684 (1993); Sawetawan, C., Bruns, E. S. and Gail, S. P., "Improvement of post-thaw motility in poor quality human semen", Fertil. Steril., 60, 706–710 (1993).

The use of the zona pellucida as a vehicle avoids the known loss in motility associated with post-thaw dilution and sperm washing seen in frozen donor semen. Verheyen, G. Pletincx, I. and Van Steirteghem, A., "Effect of freezing method, thawing temperature and post-thaw dilution/washing on motility (CASA) and morphology characteristics of high quality human sperm", Hum. Reprod., 8, 1678–1684 (1993). It is possible that the presence of multiple sperm in a small volume exerts an internally deleterious effect during freezing, thawing and centrifugation, which may be avoided by freezing sperm singly or in groups of very few cells, Aitken, R. J. and Clarkson, J. S., "Significance of reactive oxygen species and antioxidants in defining the efficacy of sperm preparation techniques", J. Androl. 9, 367–376 (1988); Mortimer, D. and Mortimer, S. T., "Methods of sperm preparation for assisted reproduction", Ann. Acad. Med. Sing., 21, 517–524 (1992).

The differences between the method according to the present invention and conventional variations of whole semen or sperm preparation freezing do not apply to altered tail characteristics. A proportion of the sperm cells frozen inside the zona pellucida exhibited tail coiling, Pedersen, H. and Lebech, P. E., "Ultrastructural changes in the human spermatozoon after freezing for artificial insemination", Fertil. Steril., 22, 125–133 (1971), but this did not inhibit their ability to fertilize after ICSI.

The method according to the present invention may be used to cryopreserve any remaining spermatozoa and even precursor cells after ICSI from highly enriched sperm suspensions of surgically treated azoospermic men. Silber, S. J., Van Steirteghem, A. C., Liu, J., Nagy, Z., Tournaye, H. and Devroey, P., "High fertilization and pregnancy rate after intracytoplasmic sperm injection with spermatozoa from testicle biopsy", *Hum. Reprod.,* 10, 148–152 (1995a); Silber, S. J., Nagy, Z., Liu, J., Tournaye, H., Lissens, W., Ferec, C., Liebaers, I., Devroey P. and Van Steirteghem, A. C., "The use of epididymal and testicular spermatzoa for intracytoplasmic sperm injection: the genetic implications for male infertility", *Hum. Reprod.,* 10, 2031–2043 (1995b); Hovatta, O., Moilanen, J., Von Schmitten, K. and Reima, I., "Testicular needle biopsy, epididymal aspiration and intracytoplasmic sperm injection in obstructive azoospermia", *Hum. Reprod.,* 10, 2595–2599 (1995); Fishel, S., Aslam, I. And Tesarik, J., "Spermatid conception: a stage too early, or a time too soon?", *Hum. Reprod.* 11, 1371–1376 (1996). Ejaculated spermatozoa from men who are occasionally azoospermic could be selected and effectively aggregrated using stored human or animal zonae, avoiding the need for a surgical extraction procedure or preventing a failed ICSI attempt due to unexpected sperm absence. The method according to the present invention makes it feasible to perform surgical extractions independently from the time and place of egg retrieval. Also, a distinct advantage of this method is that animal zonae such as those from the mouse and hamster can be used for storage.

It should be understood that the preferred embodiments and examples described herein are for illustrative purposes only and are not to be construed as limiting the scope of the present invention, which is properly delineated only in the appended claims.

What is claimed is:

1. A storage system for preservation of a sperm precursor cell or spermatozoa, comprising in combination a mammalian zona pellucida, absent an oocyte or embryonic contents, and a sperm precursor cell or spermatozoa disposed inside said zona pellucida.

2. The storage system according to claim 1, wherein said mammalian zona pellucida is formed by a process of inserting a micropipette through said zona pellucida to form an aperture and removing cellular material therethrough.

3. The storage system according to claim 2, wherein said mammalian zona pellucida is further formed by a process of, prior to inserting said micropipette and removing cellular material, forming an equalization aperture in said zona pellucida allowing pressure equalization between an interior and exterior space.

4. The storage system according to claim 1, wherein said mammalian zona pellucida is formed by a process of inserting a micropipette through said zona pellucida to form an aperture, and pressurizing the zona pellucida with fluid through said micropipette, expelling cellular material through said aperture adjacent to said micropipette.

5. The storage system according to claim 1, wherein said zona pellucida is substantially spherical, having an aqueous medium therein.

6. The storage system according to claim 1, wherein said zona pellucida is modified by action of a protease.

7. The storage system according to claim 1, wherein a spermatozoa is disposed inside said zona pellucida.

8. The storage system according to claim 1, wherein the zona pellucida holds less than about 100 cells.

9. The storage system according to claim 1, wherein said zona pellucida is bathed in a cryopreservative.

10. The storage system according to claim 1, wherein a spermatogenic cell is disposed inside said zona pellucida.

11. A method of storing individual spermatozoa, comprising the steps of:

(a) providing a zona pellucida, absent an oocyte or embryonic contents; and (b) inserting at least one sperm precursor cell or spermatozoa into said zona pellucida.

12. The method according to claim 11, further comprising the step of cryopreserving said sperm precursor cell or spermatozoa within said zona pellucida.

13. The method according to claim 11, further comprising the step of inserting a plurality of spermatozoa within a single zona pellucida.

14. The method according to claim 11, wherein said single zona pellucida contains less than 100 spermatozoa.

15. The method according to claim 11, wherein said single zona pellucida contains 5 or fewer spermatozoa.

16. The method according to claim 11, further comprising the step of washing an interior space of said zona pellucida before inserting said sperm precursor cell or spermatozoa.

17. The method according to claim 11, wherein said sperm precursor cell or spermatozoa is inserted with a micropipette.

18. The method according to claim 17, wherein said removed sperm precursor cell or spermatozoa is subsequently used to fertilize an oocyte.

19. The method according to claim 18, wherein said sperm precursor cell or spermatozoa fertilizes said oocyte by intracytoplasmic sperm injection.

20. The method according to claim 11, further comprising the step of removing said sperm precursor cell or spermatozoa from said zona pellucida.

21. The method according to claim 20, wherein said sperm precursor cell or spermatozoa is removed with a micropipette.

22. The method according to claim 11, further comprising the steps of (c) cryopreserving said sperm precursor cell or spermatozoa within said zona pellucida;

(d) thawing said cryopreserved sperm precursor cell or spermatozoa;

(e) removing said sperm precursor cell or spermatozoa from said zona pellucida; and (f) fertilizing an oocyte with said removed sperm precursor cell or spermatozoa.

23. A method of storing sperm precursor cell or spermatozoa for retrieval, comprising the steps of:

(a) isolating a fertilized or unfertilized mammalian oocyte having a zona pellucida;

(b) removing a corona radiata surrounding the oocyte;

(c) removing cellular contents from the oocyte; and (d) inserting a sperm precursor cell a spermatozoa into the acellular zona pellucida.

24. The method according to claim 23, further comprising the step of removing the sperm precursor cell or spermatozoa from the zona pellucida.

25. The method according to claim 23, further comprising the step of cryopreserving the sperm precursor cell or spermatozoa inside the zona pellucida.

* * * * *